United States Patent

Rose et al.

Patent Number: 4,745,652
Date of Patent: May 24, 1988

[54] NEW TETRA-AMINOPYRIMIDINE DERIVATIVES AND THEIR USE IN HAIR-DYEING PREPARATIONS

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 79,196

[22] Filed: Jul. 29, 1987

[30] Foreign Application Priority Data

Aug. 18, 1986 [DE] Fed. Rep. of Germany ....... 3627922

[51] Int. Cl.$^4$ ............................................. A61K 7/13
[52] U.S. Cl. .......................................... 8/409; 8/423; 544/333; 544/335
[58] Field of Search ................... 8/409, 423; 544/333, 544/297, 335

[56] References Cited

U.S. PATENT DOCUMENTS

Re. 30,199  1/1980  Rose et al. ............................... 8/409
4,213,758  7/1980  Rose et al. ............................... 8/409

Primary Examiner—Paul Lieberman
Assistant Examiner—Christine Skane
Attorney, Agent, or Firm—Ernest G. Szoke; Henry E. Millson, Jr.

[57] ABSTRACT

New 2,4,5,6-tetra-aminopyrimidine derivatives corresponding to the following general formula

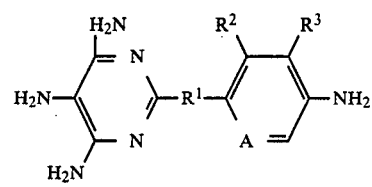

in which $R^1$ is a group of the formula —NH—$(CH_2)_n$—NH—, where $n=2-4$, a group of the formula —NH—$CH_2$—CH(OH)—$CH_2$—NH— or a group of the formula

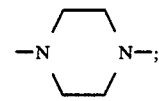

$R^2$ and $R^3$ independently of one another represent hydrogen, chlorine or a group of the formula —$OR^4$ where $R^4$ is a $C_1$–$C_4$ alkyl group and A is a CH group or a nitrogen atom, and salts thereof. The compounds are suitable as developer components for oxidation hair dyes which, in conjunction with a number of standard coupler compounds, form a wide range of brilliant colors with high absorptive power on human hair and good fastness properties.

15 Claims, No Drawings

NEW TETRA-AMINOPYRIMIDINE DERIVATIVES AND THEIR USE IN HAIR-DYEING PREPARATIONS

BACKGROUND OF THE INVENTION

1. Field of the Invention

This invention relates to new pyrimidine compounds, including derivatives of 2,4,5,6-tetra-aminopyrimidine, and salts thereof, and to their use as developer component in oxidation hair-dyeing preparations.

So-called oxidation hair-dye preparations play a prominent part in the dyeing of hair by virtue of their intensive colors and good fastness properties. Hair-dyeing preparations of this type contain oxidation dye precursors in a cosmetic carrier. Developer substances and coupler substances are used as oxidation dye precursors. Under the effect of oxidizing agents or atmospheric oxygen, the developer components from the actual dyes either in conjunction with one another or through coupling with one or more coupler components.

A certain developer substance is also capable of forming very different shades by combination with different couplers. In spite of this, it is often not possible to achieve the variety of natural hair colors with one and the same developer substance. In practice, therefore, it is generally necessary to combine various developer components and coupler components to obtain a single, natural-looking hair color.

Good oxidation dye precursors have to satisfy above all the following requirements. Thus, they have to form the required shades with sufficient intensity and fastness during the oxidative coupling reaction. In addition, they must be readily absorbed by human hair with no significant differences between mismanaged hair and freshly washed hair. They are required to be stable to light, heat and the effect of chemical reducing agents, for example permanent wave lotions. Finally, they should not overly stain the scalp and, above all, should be safe to use from the toxicological and dermatological viewpoint.

The developer substances normally used are primary aromatic amines containing another free or substituted hydroxy or amino group in the para position or ortho position, also diaminopyridine derivatives, heterocyclic hydrazone derivatives and 4-aminopyrazolone derivatives. The so-called couplers used include m-phenylenediamine derivatives, naphthols, resorcinol derivatives and pyrazolones.

The use of 2,4,5,6-tetra-aminopyrimidines as a developer component in hair dyeing preparations was known from U.S. Re. No. 30,199. The 2,4,5,6-tetra-aminopyrimidine derivatives described therein give only a limited range of shades with a number of couplers, primarily among the yellows, browns and reds.

The present invention relates to new 2,4,5,6-tetra-aminopyrimidine derivatives corresponding to the following formula

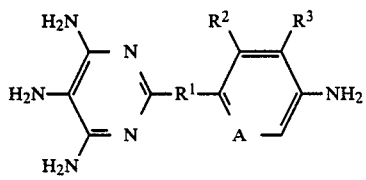  (I)

in which $R^1$ is a group of the formula $-NH-(CH_2)_n-NH-$, where $n=2-4$, a group of the formula $-NH-CH_2-CH(OH)-CH_2-NH-$ or a group of the formula

$R^2$ and $R^3$, which may be the same or different, independently of one another represent hydrogen, chlorine or a group of the formula $-OR^4$, where $R^4$ is a $C_1-C_4$ alkyl group, and A is a CH group or a nitrogen atom, and to the salts thereof.

These new 2,4,5,6-tetra-aminopyrimidine derivatives corresponding to formula I are oxidation dye precursors of the developer substance type, i.e. they are capable of forming dyes under the effect of oxidizing agents. In the presence of coupler substances, however, particularly bright and intense colors are formed. Suitable coupler substances are, above all, the m-phenylenediamines, m-aminophenols, resorcinols, 1-naphthol, 1,5- and 2,6-dihydroxynaphthalene, hydroxy and aminopyridines, hydroxy-quinolines and aminopyrazolones. With these and other known coupler substances, the 2,4,5,6-tetra-aminopyrimidine derivatives according to the invention form a wide range of colors extending from orange-yellow to deep blue. Above all, however, colors which would otherwise only be obtainable using two or more different developers can be produced with many couplers. Accordingly, the 2,4,5,6-tetra-aminopyrimidine derivatives of formula I according to the invention are eminently suitable for use as oxidation dye precursors of the developer type in hair dyeing preparations. Hair dyeing preparations containing the 2,4,5,6-tetra-aminopyrimidine derivatives according to the invention, as the developer component in addition to standard coupler components, show particularly uniform absorption both on mismanaged hair and on freshly washed hair. The dye finishes obtained show high stability to heat. Preference is attributed, particularly by virtue of their ready availability to the 2,4,5,6-tetra-aminopyrimidine derivatives of formula I in which $R^2$ and $R^3$ are hydrogen where A is a nitrogen atom and in which at least one of the groups $R^2$ and $R^3$ is hydrogen where A is a CH group. By virtue of their high molecular weight, the new 2,4,5,6-tetra-aminopyrimidine derivatives are substantially nonresorbable which favorably affects their toxicological and dermatological properties.

The 2,4,5,6-tetra-aminopyrimidine derivatives of formula I according to the invention may be prepared by reacting under reflux conditions compounds corresponding to the following formula

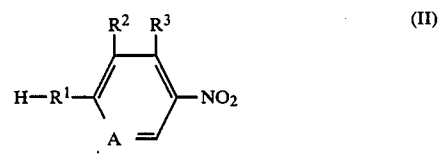  (II)

with a 2-alkylmercapto-4,6-diamino-5-nitrosopyrimidine in which the alkyl group contains 1–4 carbon atoms, such as 2-methylmercapto-4,6-diamino-5-nitrosopyrimidine, and catalytically hydrogenating the compounds obtained (intermediate stage) corresponding to the following formula

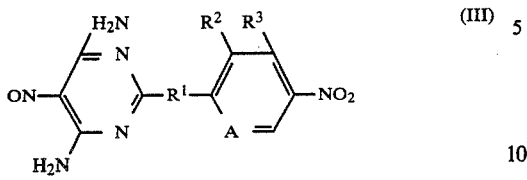

In formulae II and III, $R^1$, $R^2$, $R^3$ and A have the same meanings as in formula I.

In the catalytic hydrogenation, the usual catalysts are employed using nickel (Raney nickel) platinum or palladium on a support or carrier, preferably platinum or palladium on carbon, with hydrogen under pressure.

The 2,4,5,6-tetra-aminopyrimidine derivatives according to the invention may be isolated and used in hair dyeing preparations either as such or in the form of their salts with inorganic or organic acids, for example as hydrochlorides, sulfates, phosphates, acetates, propionates, lactates or citrates.

The present invention also relates to hair dyeing preparations containing oxidation dye precursors in a cosmetic carrier which contain as oxidation dye precursors 2,4,5,6-tetra-aminopyrimidine derivatives of formula I as developer component in a quantity of from 0.05 to 10 millimoles per 100 g of hair dye preparation in addition to standard coupler components and, optionally, substantive hair dyes.

In the hair dyes according to the invention, the developer substances and the coupler substances are generally used in equimolar quantities, although a certain excess of individual oxidation dye precursors is not a disadvantage, so that developer substances and coupler substances may be used in a molar ratio of from 1:0.5 to 1:2, more desirably from 1:0.75 to 1:1.25. With a slight excess of the coupler compound, the hair dyeing preparations according to the invention form slightly more intense colors. There is no need for the 2,4,5,6-tetra-aminopyrimidine derivatives corresponding to formula I to be used as individual compounds. Instead, mixtures of these compounds may also be used.

To modify the hair color, known substantive hair dyes, for example nitrophenylenediamine derivatives, anthraquinone dyes or indophenols, may also be added to the hair dyeing preparations according to the invention.

To produce the hair dyeing preparations according to the invention, the oxidation dye precursors and, optionally, substantive dyes are incorporated in a suitable cosmetic carrier. Carriers such as these are, for example, creams, emulsions, gels or even surfactant-containing foaming solutions, for example shampoos, or other preparations which are suitable for application to the hair. Standard constituents of cosmetic preparations, such as these are, for example, wetting agents and emulsifiers, such as anionic, nonionic or ampholytic surfactants, for example fatty alcohol sulfates, alkane sulfonates, α-olefin sulfonates, fatty alcohol polyglycol ether sulfates, ethylene oxide adducts with fatty alcohols, fatty acids and alkylphenols, sorbitan fatty acid esters and fatty acid partial glycerides, and fatty acid alkanolamides. Also thickeners are included such as, for example, methyl or hydroxyethyl cellulose, starch, fatty alcohols, paraffin oils, fatty acids. Also often added are perfume oils and hair-care additives such as, for example, water-soluble cationic polymers, protein derivatives, pantothenic acid and cholesterol.

The constituents of the cosmetic carriers are used in the usual quantities for producing the hair dyeing preparations according to the invention. For example, emulsifiers are used in concentrations of from 0.5 to 30%, usually about 5-20%, by weight and thickeners in concentrations of from 0.1 to 25%, usually about 1-10%, by weight, based on the preparations as a whole. The oxidation dye precursors are incorporated in the carrier in quantities of from 0.2 to 5% by weight and preferably in quantities of from 1 to 3% by weight, based on the preparation as a whole.

In principle, the dye may be oxidatively developed with air. However, it is preferred to use a chemical oxidizing agent, particularly when, in addition to dyeing, the hair is also to be lighted. Suitable oxidizing agents are, in particular, hydrogen peroxide or adducts thereof with urea, melamine or sodium borate and also mixtures of these hydrogen peroxide adducts with potassium peroxydisulfate.

The hair dyeing preparations according to the invention may be used in a mildly acidic, neutral or alkaline medium, irrespective of the cosmetic carrier used, for example a cream, gel or shampoo. The hair dyeing preparations are preferably used in the pH range from 8 to 10. They may be used at temperatures of from 15° C. to 40° C.

After a contact time of about 30 minutes, the hair dyeing preparation is removed by rinsing from the hair to be dyed. The hair is then washed with a mild shampoo and dried. Washing with a shampoo is unnecessary when a carrier of high surfactant content, for example a dye shampoo, is used.

The following Examples are intended to illustrate the invention without limiting it in any way.

EXAMPLES

1. Production Examples

General procedure:

Step 1

A mixture of 0.05 mole of the compound corresponding to formula II and 0.05 mole 2-methylmercapto-4,6-diamino-5-nitrosopyrimidine was refluxed for 5 hours in 500 ml ethanol. After cooling to 20° C., the intermediate product of formula III was filtered off and dried in a drying cabinet at 80° C.

Step 2

5 g of the intermediate product of formula III were dissolved in 200 ml ethanol and, after addition of 0.5 g palladium on active carbon (10%), the resulting solution was catalytically hydrogenated at 20° C. and 2 bar hydrogen pressure. After the uptake of hydrogen had stopped. the catalyst was filtered off, the filtrate was acidified with concentrated hydrochloric acid and concentrated by evaporation to dryness. The 2,4,5,6-tetra-aminopyrimidine derivative of formula I was obtained.

The following compounds were prepared by this general procedure (Table 1)

TABLE 1

| Compound of formula I | R¹ | R² | R³ | A |
|---|---|---|---|---|
| 1.1 | —NH—(CH$_2$)$_2$—NH— | H | H | CH |
| 1.2 | —NH—(CH$_2$)$_3$—NH— | H | H | CH |
| 1.3 | —NH—(CH$_2$)$_4$—NH— | H | H | CH |
| 1.4 | —NH—CH$_2$—CH—(OH)—CH$_2$—NH— | H | H | CH |
| 1.5 | —NH—(CH$_2$)$_2$—NH— | Cl | H | CH |
| 1.5 | —NH—(CH$_2$)$_2$—NH— | H | OCH$_3$ | CH |
| 1.7 | —N⟨piperazine⟩N— | H | H | CH |
| 1.8 | —NH—(CH$_2$)$_2$—NH— | H | H | N |

Chemical names of compounds 1.1 to 1.8, their appearance and melting points, the starting compounds (II) from which they were prepared and the intermediate stages (III) obtained:

1.1  2-[2-(p-aminoanilino)-ethylamino]-4,5,6-diaminopyrimidine tetrahydrochloride
light yellow crystals, metling point 187° C. (with decomposition) starting compound (II)
N-(p-nitrophenyl)-ethylenediamine intermediate stage (III)
2-[2-(p-nitroanilino)-ethylamino]-4,6-diamino-5-nitrosopyrimidine orange crystals, melting point 279°–282° C.

1.2  2-[3-(p-aminoanilino)-propylamino]-4,5,6-triaminopyrimidine tetrahydrochloride
colorless cyrstals, melting point 180° C. (with decomposition) starting compound (II)
N-(p-nitrophenyl)-trimethylenediamine intermediate stage (III)
2-[3-(p-nitroanilino)-propylamino]-4,6-diamino-5-nitrosopyrimidine orange-brown crystals, melting point 263° C.

1.3  2-[4-(p-aminoanilino)-butylamino]-4,5,6-triaminopyrimidine tetrahydrochloride
colorless crystals, melting point beyond 170° C. (with decomposition)
starting compound (II)
N-(p-nitrophenyl)-tetramethylenediamine intermediate stage (III)
2-[4-(p-nitroanilino)-butylamino]-4,6-diamino-5-nitrosopyrimidine ochre-colored crystals, melting point 210°–216° C.

1.4  2-[-(p-aminoanilino)-2-hydroxypropylamino]-4,5,6-triaminopyrimidine tetrahydrochloride
beige crystals, melting point beyond 175° C. (with decomposition)
starting compound (II)
N-(p-nitrophenyl)-2-hydroxy-1,3-diaminopropane intermediate stage (III)
2-[3-(p-nitroanilino)-2-hydroxypropylamino]-4,6-diamino-5-nitrosopyrimidine
orange-brown crystals, melting point 236°–246° C.

1.5  2-[2-(2-chloro-4-aminoanilino)-ethylamino]-4,5,6-triaminopyrimidine tetrahydrochloride
starting compound (II)
N-(O-cholor-p-nitrophyenl)-ethylenediamine intermediate stage (III)
2-[2-(2-chloro-4-nitroanilino)-ethylamino]-4,6-diamino-5-nitrosopyrimidine
orange-yellow crystals, melting point beyond 258° C. (with decomposition)

1.6  2-[2-(3-methoxy-4-aminoanilino)-ethylamino]-4,5,6-triaminopyrimidine tetrahydrochloride
starting compound (II)
N-(4-nitro-3-methoxyphenyl)-ethylenediamine intermediate stage (III)
2-[2-(3-methoxy-4-nitroanilino)-ethylamino]-4,6-diamino-5-nitrosopyrimidine
ochre-colored crystals, melting point beyond 205° C. (with decomposition)

1.7  2-[4-p-aminophenylpiperazin-(1)-yl]-4,5,6-triaminopyrimidine tetrahydrochloride
yellow crystals, melting point beyond 190° C.
starting compound (I)
1-(4-nitrophenyl)-piperazine
intermediate stage (III)
2-[4-p-nitrophenylpiperazin-(1)-yl]-4,6-diamino-5-nitrosopyrimidine
red crystals, melting point 283°–289° C.

1.8  2-[2-(5-aminopyridyl-(2)-amino)-ethylamino]-4,5,6-triaminopyrimidine tetrahydrochloride
beige crystals, melting point beyond 178° C. (with decomposition)
starting compound (II)
2-(β-aminoethylamino)-5-nitropyridine intermediate stage (III)
2-[2-(5-nitropyridyl-(2)-amino)-ethylamino]-4,6-diamino-5-nitrosopyrimidine
orange crystals, melting point above 310° C.

2. Application Examples

Hair dyeing preparations according to the invention were prepared in the form of a hair dyeing cream emulsion having the following composition:

| | |
|---|---|
| C$_{12}$–C$_{14}$ fatty alcohol | 10.0 g |
| C$_{12}$–C$_{14}$ fatty alcohol + 2 EO sulfate, Na salt, 28% | 25.0 g |
| Water | 60.0 g |
| Tetra-aminopyrimidine derivative | 7.5 mmoles |
| Coupler component | 7.5 mmoles |
| Na$_2$SO$_3$ (inhibitor) | 1.0 g |
| Concentrated ammonia solution | to pH = 9.5 |
| Water | to 100 g |

The constituents were mixed with one another in the above order. After addition of the oxidation dye precursors and the inhibitor, the pH value of the emulsion was first adjusted to 9.5 with concentrated ammonia solution, after which the emulsion was made up with water to 100 g.

The dye was oxidatively developed with 3% hydrogen peroxide solution as oxidizing agent. To this end, 50 g hydrogen peroxide solution (3%) were added to and mixed with 100 g of the emulsion.

The dyeing cream was applied to approximately 5 cm long strands of standardized, 90% grey, but otherwise not specially pretreated human hair and left thereon for 30 minutes at 27° C. At the end of the dyeing process, the hair was rinsed, washed with a standard shampoo and then dried.

The tetra-aminopyrimidine derivatives of Examples 1.1 to 1.8 were used as developers. The following compounds were used as coupler components:
2.1 1-naphthol
2.2 2,4-diaminophenoxyethanol
2.3 2,4-diaminophenetol
2.4 2-chloro-6-methyl-3-aminophenol
2.5 1,3-bis-(2,4-diaminophenoxy)-propane
2.6 2,4-dichloro-3-aminophenol
2.7 5-amino-2-methylphenol
2.8 5-amino-4-chloro-2-methylphenol
2.9 m-aminophenol
2.10 1-phenyl-3-amino-5-pyrazolone
2.11 3-amino-2-methylamino-6-methoxypyridine
2.12 6-hydroxyquinoline
2.13 2,6-dihydroxy-3,4-dimethylpyridine
2.14 2,7-dihydroxynaphthalene
2.15 2,6-dihydroxypyridine
2.16 2-amino-3-hydroxypyridine
2.17 4,6-dichlororesorcinol
2.18 2-methyl resorcinol The hair colors obtained with the oxidation dye precursors, mentioned above are shown in Table II

TABLE II

| Application Example | Developer component | Coupler component | Color obtained |
|---|---|---|---|
| A1 | 1.1 | 2.1 | matt blue |
| A2 | 1.1 | 2.2 | dark blue |
| A3 | 1.1 | 2.3 | dark blue |
| A4 | 1.1 | 2.6 | grey-blue |
| A5 | 1.1 | 2.8 | dark violet |
| A6 | 1.1 | 2.9 | dark violet |
| A7 | 1.1 | 2.10 | mahogany red |
| A8 | 1.1 | 2.11 | dark green |
| A9 | 1.1 | 2.12 | olive |
| A10 | 1.1 | 2.13 | olive |
| A11 | 1.1 | 2.14 | olive-yellow |
| A12 | 1.1 | 2.15 | olive-brown |
| A13 | 1.1 | 2.16 | grey-brown |
| A14 | 1.1 | 2.17 | red-brown |
| A15 | 1.2 | 2.4 | dark blue |
| A16 | 1.2 | 2.14 | bronze-brown |
| A17 | 1.2 | 2.18 | burgundy red |
| A18 | 1.3 | 2.4 | dark blue |
| A19 | 1.3 | 2.14 | hair brown |
| A20 | 1.3 | 2.18 | burgundy red |
| A21 | 1.4 | 2.5 | matt blue |
| A22 | 1.4 | 2.7 | grey-ruby |
| A23 | 1.4 | 2.13 | olive |
| A24 | 1.4 | 2.14 | olive |
| A25 | 1.5 | 2.7 | grey-blue |
| A26 | 1.5 | 2.14 | yellow-brown |
| A27 | 1.5 | 2.18 | grey-ruby |
| A28 | 1.6 | 2.8 | grey-blue |
| A29 | 1.6 | 2.10 | grey-violet |
| A30 | 1.7 | 2.6 | grey-blue |
| A31 | 1.7 | 2.9 | grey-violet |
| A32 | 1.8 | 2.1 | grey-blue |
| A33 | 1.8 | 2.18 | grey-brown |

What is claimed:

1. A pyrimidine compound selected from the group consisting of a 2,4,5,6-tetra-aminopyrimidine having the formula

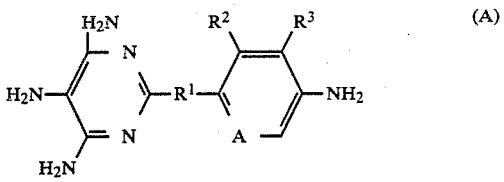

and a pyrimidine having the formula

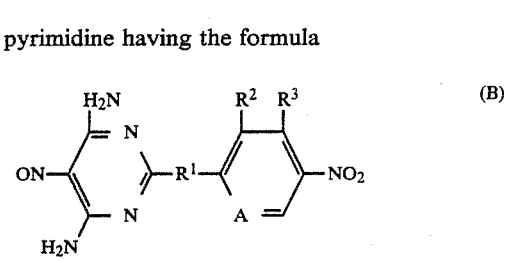

in which $R^1$ is selected from the group consisting of —NH—$(CH_2)_n$—NH— where n is an integer of 2–4, —NH—$CH_2$—CH(OH)—$CH_2$—NH— and

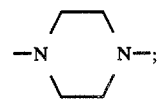

$R^2$ and $R^3$ which may be the same or different, independently of one another are hydrogen, chlorine or —$OR^4$, where $R^4$ is a $C_1$–$C_4$ alkyl group, and A is CH or a nitrogen atom.

2. A pyrimidine compound as defined in claim 1 wherein $R^2$ and $R^3$ are hydrogen where A is a nitrogen atom and in that at least one of the groups $R^2$ and $R^3$ is hydrogen where A is a CH group.

3. A pyrimidine compound as defined in formula (B) of claim 1 and is selected from the groups of
 (a) 2-[2-(p-nitroanilino)-ethylamino]-4,6-diamino-5-nitrosopyrimidine
 (b) 2-[3-(p-nitroanilino)-propylamino]-4,6-diamino-5-nitrosopyrimidine
 (c) 2-[4-(p-nitroanilino)-butylamino]-4,6-diamino-5-nitrosopyrimidine
 (d) 2-[3-(p-nitroanilino)-2-hydroxypropylamino]-4,6-diamino-5-nitrosopyrimidine
 (e) 2-[2-(2-chloro-4-nitroanilino)-ethylamino]-4,6-diamino-5-nitrosopyrimidine
 (f) 2-[2-(3-methoxy-4-nitroanilino)-ethylamino]-4,6-diamino-5-nitrosopyrimidine
 (g) 2-[4-p-nitrophenylpiperazin-(1)-yl]-4,6-diamino-5-nitrosopyrimidine
 (h) 2-[2-(5-nitropyridyl-(2)-amino)-ethylamino]-4,6-diamino-5-nitrosopyrimidine.

4. The acid salt of a 2,4,5,6-tetra-aminopyrimidine compound as defined in formula (A) of claim 1 wherein said acid is an inorganic acid selected from the group consisting of hydrochloric, sulfuric and phosphoric acid.

5. The tetrahydrochloride salt of a 2,4,5,6-tetra-aminopyrimidine compound defined in formula (A) of claim 1 and is selected from the group consisting of
 (a) 2-[2-(p-aminoanilino)-ethylamino]-4,5,6-diaminopyrimidine tetrahydrochloride
 (b) 2-[3-(p-aminoanilino)-propylamino]-4,5,6-triamino-pyrimidine tetrahydrochloride (c) 2-[4-(p-aminoanilino)-butylamino]-4,5,6-triamino-pyrimidine tetrahydrochloride
(d) 2-[3-(p-aminoanilino)-2-hydroxy-propylamino]4,5,6-triamino pyrimidine tetrahydrochloride
(e) 2-[2-(2-chloro-4-aminoanilino)-ethylamino]-4,5,6-triamino pyrimidine tetrahydrochloride
(f) 2-[2-(3-methoxy-4-aminoanilino)-ethylamino]-4,5,6-triamino pyrimidine tetrahydrochloride
(g) 2-[4-p-aminophenylpiperazin-(1)-yl]-4,5,6-triamino-pyrimidine tetrahydrochloride
(h) 2-[2-(5-aminopyridyl-(2)-amino)-ethylamino]-4,5,6-triamino pyrimidine tetrahydrochloride.

6. The organic acid salt of a 2,4,5,6-tetra-aminopyrimidine compound as defined in formula (A) of claim 1 wherein said acid is selected from the group consisting of acetic, propionic, lactic and citric acid.

7. A process of the production of a 2,4,5,6-tetra-amino-pyrimidine having the general formula

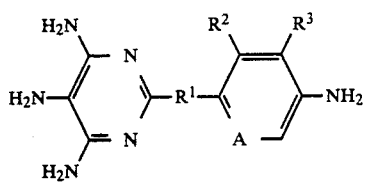

(I)

in which R¹ is selected from the group of—NH—(CH₂)ₙ—NH—, where n is an integer of 2-4, —NH—CH₂—CH(OH)—CH₂—NH— or

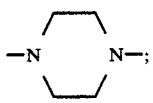

R² and R³, which may be the same or different, independently of one another are hydrogen, chlorine or —OR⁴, where R⁴ is a C₁-C₄ alkyl group, and A is a CH group or a nitrogen atom, comprising reacting with a 2-alkyl-mercapto-4,6-diamino-5-nitrosopyrimidine in which the alkyl group contains from 1-4 carbon atoms, a compound of the formula

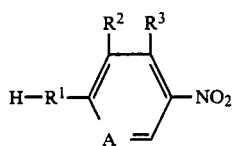

(II)

thereby providing a pyrimidine compound of the formula

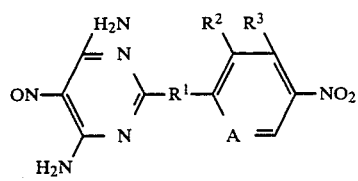

(III)

wherein R¹, R², R³ and A are as defined above and catalyticaly hydrogenating said compound III providing said 2,4,5,6-tetra-aminopyrimidine.

8. A process as defined in claim 7 wherein said 2-alkylmercapto-4,6-diamino-5-nitrosopyrimidine is 2-methylmercapto-4,6-diamino-5-nitrosopyrimidine.

9. A process as defined in claim 8 wherein said hydrogenation is conducted in the presence of a catalyst selected from the group consisting of Raney nickel, palladium and platinum.

10. A process as defined in claim 9 in which said catalyst is palladium on carbon.

11. In a hair dyeing preparation containing an oxidation dye precursor in a cosmetic carrier, the improvement wherein said oxidation dye precursor is the 2,4,5,6-tetra-aminopyrimidine defined in formula (A) of claim 1.

12. A hair dyeing preparation as defined in claim 11 wherein said 2,4,5,6-tetra-aminopyrimidine compound is present in an amount of from 0.05–1-millimoles per 100 grams of hair dyeing preparation.

13. A hair dyeing preparation as defined in claim 11 wherein said 2,4,5,6-tetra-aminopyrimidine oxidation dye precursor is selected from the group consisting of
(a) 2-[2-(p-aminoanilino)-ethylamino]-4,5,6-diamino-pyrimidine tetrahydrochloride
(b) 2-[3-(p-aminoanilino)-propylamino]-4,5,6-triamino-pyrimidine tetrahydrochloride
(c) 2-[4-(p-aminoanilino)-butylamino]-4,5,6-triamino-pyrimidine tetraphydrohloride
(d) 2-[3-(p-aminoanilino)-2-hydroxy-propylamino] 4,5,6-triamino pyrimidine tetrahydrochloride
(e) 2-[2-(2-chloro-4-aminoanilino)-ethylamino]-4,5,6-triamino pyrimidine tetrahydrochloride
(f) 2-[2-(3-methoxy-4-aminoanilino)-ethylamino]-4,5,6-triamino pyrimidine tetrahydrochloride
(g) 2-[4-p-aminophenylpiperazin-(1)-yl]-4,5,6triamino-pyrimidine tetrahydrochloride
(h) 2-[2-(5-aminopyridyl-(2)-amino)-ethylamino]-4,5,6-triamino pyrimidine tetrahydrochloride.

14. A hair dyeing preparation as defined in claim 13 and further comprising a coupler component.

15. A hair dyeing preparation as defined in claim 14 wherein said coupler component is selected from the group consisting of
(1) 1-naphthol
(2) 2,4-diaminophenoxyethanol
(3) 2,4-diaminophenetol
(4) 2-chloro-6-methyl-3-aminophenol
(5) 1,3-bis-(2,4-diaminophenoxy)-propane
(6) 2,4-dichloro-3-aminophenol
(7) 5-amino-2-methylphenol
(8) 5-amino-4-chloro-2-methylphenol
(9) m-aminophenol
(10) 1-phenyl-3-amino-5-pyrazolone
(11) 3-amino-2-methylamino-6-methoxypyridine
(12) 6-hydroxyquinoline
(13) 2,6-dihydroxy-3,4-dimethylpyridine
(14) 2,7-dihydroxynaphthalene
(15) 2,6-dihydroxypyridine
(16) 2-amino-3-hydroxypyridine
(17) 4,6-dichlororesorcinol
(18) 2-methyl resorcinol.

* * * * *